US010022485B2

(12) United States Patent
Peters et al.

(10) Patent No.: US 10,022,485 B2
(45) Date of Patent: Jul. 17, 2018

(54) DEVICE AND METHOD FOR MONITORING AN EXTRACORPOREAL BLOOD TREATMENT

(75) Inventors: Arne Peters, Bad Homburg (DE); Christoph Wiktor, Gelnhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 505 days.

(21) Appl. No.: 13/519,223

(22) PCT Filed: Dec. 27, 2010

(86) PCT No.: PCT/EP2010/007948
§ 371 (c)(1),
(2), (4) Date: Aug. 17, 2012

(87) PCT Pub. No.: WO2011/079941
PCT Pub. Date: Jul. 7, 2011

(65) Prior Publication Data
US 2012/0330214 A1    Dec. 27, 2012

(30) Foreign Application Priority Data

Dec. 28, 2009 (DE) .................. 10 2009 060 668

(51) Int. Cl.
*A61M 1/14* (2006.01)
*A61M 1/36* (2006.01)
*A61M 1/16* (2006.01)

(52) U.S. Cl.
CPC ........ *A61M 1/3663* (2013.01); *A61M 1/1603* (2014.02); *A61M 1/3656* (2014.02); *A61M 2205/18* (2013.01); *A61M 2205/3375* (2013.01)

(58) Field of Classification Search
USPC ........................................ 604/6.11
See application file for complete search history.

(56) References Cited

U.S. PATENT DOCUMENTS

| 4,093,545 A | 6/1978 | Cullis |
| 4,334,988 A | 6/1982 | Milligan |

(Continued)

FOREIGN PATENT DOCUMENTS

| DE | 25 52 755 A1 | 8/1976 |
| DE | 693 05 438 T2 | 4/1997 |

(Continued)

OTHER PUBLICATIONS

PCT International Search Report from PCT/EP2010/007948, dated May 19, 2011.

(Continued)

*Primary Examiner* — Todd J Scherbel
*Assistant Examiner* — Guy K Townsend
(74) *Attorney, Agent, or Firm* — Kilyk & Bowersox, P.L.L.C.

(57) ABSTRACT

A device and method for monitoring an access to a patient, an extracorporeal blood circuit and/or a dialyzing fluid system includes a centrifugal pump for conveying blood or dialyzing fluid instead of an occluding pump. Centrifugal pumps bring about a large change in flow rate by even a small change in pressure difference across the pump. The device includes a measuring unit for measuring the flow rate of blood or dialyzing fluid conveyed by the centrifugal pump, and a control and computing unit configured to determine an incorrect vascular access or malfunction if a change in measured flow rate Q is more than a predetermined amount. For example, a small drop in pressure in the venous blood line leads to a marked increase in the flow rate of the centrifugal pump, which is used as a basis for the detection of an incorrect vascular access.

17 Claims, 2 Drawing Sheets

(56) References Cited

U.S. PATENT DOCUMENTS

| | | | |
|---|---|---|---|
| 4,739,492 A | 4/1988 | Cochran | |
| 4,838,865 A | 6/1989 | Flank et al. | |
| 4,923,598 A | 5/1990 | Schal | |
| 4,995,268 A | 2/1991 | Ash et al. | |
| 5,091,094 A | 2/1992 | Veech | |
| 5,399,157 A | 3/1995 | Goux et al. | |
| 5,685,989 A | 11/1997 | Krivitzki et al. | |
| 6,153,109 A | 11/2000 | Krivitzki | |
| 6,167,765 B1 | 1/2001 | Weitzel | |
| 6,210,591 B1 | 4/2001 | Krivitzki | |
| 6,221,040 B1* | 4/2001 | Kleinekofort | A61M 1/16 604/4.01 |
| 6,235,199 B1* | 5/2001 | Peterson | A61M 1/1656 137/599.01 |
| 6,514,419 B2 | 2/2003 | Krivitzki | |
| 6,575,927 B1 | 6/2003 | Weitzel et al. | |
| 6,709,414 B2 | 3/2004 | Weitzel et al. | |
| 6,926,838 B2 | 8/2005 | Krivitzki et al. | |
| 7,004,924 B1* | 2/2006 | Brugger | A61M 1/3626 600/16 |
| 7,297,280 B2 | 11/2007 | Krivitzki et al. | |
| 7,473,371 B2 | 1/2009 | Krivitzki et al. | |
| 8,133,194 B2* | 3/2012 | Szamosfalvi | A61M 1/3672 210/645 |
| 8,211,048 B2* | 7/2012 | Szamosfalvi | A61M 1/3672 210/646 |
| 8,246,826 B2* | 8/2012 | Wilt | A61M 1/16 210/257.1 |
| 8,357,298 B2* | 1/2013 | Demers | A61M 1/16 210/646 |
| 8,409,441 B2* | 4/2013 | Wilt | A61M 1/16 210/636 |
| 8,425,417 B2* | 4/2013 | Leach | A61B 5/0215 600/365 |
| 8,647,290 B2* | 2/2014 | Masala | A61M 1/342 422/44 |
| 8,721,879 B2* | 5/2014 | van der Merwe | A61M 1/16 210/134 |
| 8,721,884 B2* | 5/2014 | Wilt | A61M 1/16 210/106 |
| 2001/0021817 A1 | 9/2001 | Brugger et al. | |
| 2001/0050256 A1 | 9/2001 | Brugger et al. | |
| 2003/0111423 A1 | 6/2003 | Krivitski | |
| 2003/0167030 A1 | 9/2003 | Weitzel et al. | |
| 2005/0044339 A1* | 2/2005 | Sheets | G06F 9/384 711/206 |
| 2005/0051496 A1 | 3/2005 | Krivitski | |
| 2005/0131332 A1* | 6/2005 | Kelly | A61M 1/1696 604/4.01 |
| 2005/0178732 A1 | 8/2005 | Krivitski | |
| 2007/0038191 A1* | 2/2007 | Burbank | A61M 1/1643 604/317 |
| 2008/0015487 A1* | 1/2008 | Szamosfalvi | A61M 1/3672 604/6.07 |
| 2008/0217245 A1 | 9/2008 | Rambod et al. | |
| 2009/0008331 A1* | 1/2009 | Wilt | A61M 1/16 210/647 |
| 2009/0221948 A1* | 9/2009 | Szamosfalvi | A61M 1/3672 604/6.07 |
| 2010/0192686 A1* | 8/2010 | Kamen | A61M 1/16 73/290 R |
| 2011/0208105 A1* | 8/2011 | Brandl | A61M 1/342 604/5.01 |
| 2012/0150090 A1* | 6/2012 | Szamosfalvi | A61M 1/3672 604/6.07 |
| 2012/0265116 A1* | 10/2012 | Szamosfalvi | A61M 1/3672 604/6.07 |
| 2012/0330214 A1* | 12/2012 | Peters | A61M 1/3663 604/6.11 |
| 2013/0020237 A1* | 1/2013 | Wilt | A61M 1/1037 210/85 |
| 2013/0032536 A1* | 2/2013 | Wilt | A61M 1/16 210/646 |
| 2013/0037480 A1* | 2/2013 | Wilt | A61M 1/16 210/321.69 |
| 2013/0126413 A1* | 5/2013 | van der Merwe | A61M 1/16 210/321.6 |
| 2013/0155387 A1* | 6/2013 | Wiktor | A61M 1/3626 356/39 |
| 2013/0204174 A1* | 8/2013 | Olde | A61M 1/3653 604/6.11 |
| 2013/0204542 A1* | 8/2013 | Olde | A61M 1/3653 702/35 |
| 2013/0280104 A1* | 10/2013 | Heide | F04B 43/12 417/53 |
| 2013/0304020 A1* | 11/2013 | Wilt | A61M 1/16 604/506 |
| 2014/0102970 A1* | 4/2014 | Wilt | A61M 1/16 210/321.69 |
| 2014/0221897 A1* | 8/2014 | Szamosfalvi | A61M 1/3672 604/6.07 |
| 2014/0309611 A1* | 10/2014 | Wilt | A61M 1/16 604/500 |

FOREIGN PATENT DOCUMENTS

| | | |
|---|---|---|
| DE | 26 59 377 A1 | 9/1999 |
| DE | 198 09 945 A1 | 9/1999 |
| DE | 198 48 235 C1 | 3/2000 |
| DE | 694 29 877 T2 | 11/2001 |
| EP | 0 300 201 A1 | 1/1989 |
| EP | 0 416 808 A1 | 3/1991 |
| EP | 0 943 369 A1 | 9/1999 |
| JP | H11-506682 A | 6/1999 |
| JP | 2006325750 A | 7/2006 |
| JP | 2008-023269 A | 2/2008 |
| JP | 2009-502446 A | 1/2009 |
| WO | 96/40316 | 12/1996 |
| WO | 00/018451 A1 | 4/2000 |
| WO | 00/53291 A1 | 9/2000 |
| WO | 2005/044339 A2 | 5/2005 |
| WO | 2007/019519 A2 | 2/2007 |

OTHER PUBLICATIONS

International Preliminary Report on Patentability from PCT/EP2010/007948, dated Jul. 10, 2012.

Office Action for Japanese Patent Application No. 2015-167527, issued by the Japanese Patent Office (JPO), dated Jul. 19, 2016, 3 pages.

* cited by examiner

DEVICE AND METHOD FOR MONITORING AN EXTRACORPOREAL BLOOD TREATMENT

CROSS-REFERENCE TO RELATED APPLICATIONS

The present application is the national stage entry of International Patent Application No. PCT/EP2010/007948, filed on Dec. 27, 2010, and claims priority to Application No. DE 10 2009 060 668.8, filed in the Federal Republic of Germany on Dec. 28, 2009.

FIELD OF INVENTION

The present invention relates to a device for monitoring an access to a patient for an extracorporeal blood treatment apparatus with an extracorporeal blood circuit. Moreover, the present invention relates to a device for monitoring an extracorporeal blood circuit of an extracorporeal blood treatment apparatus. Furthermore, the present invention relates to a method for monitoring a patient access and an extracorporeal blood circuit in an extracorporeal blood treatment. The present invention also relates to an extracorporeal blood treatment apparatus with a monitoring device.

BACKGROUND INFORMATION

In the field of medical technology, various extracorporeal blood treatment apparatuses comprising an extracorporeal blood circuit are known. The known extracorporeal blood treatment apparatuses include for example haemodialysis apparatuses and cell separators, which necessitate an access to the patient's vascular system. In extracorporeal blood treatment, blood is removed from the patient with an arterial puncture cannula via an arterial hose line, the blood being fed back to the patient with a venous puncture cannula via a venous hose line.

In order to convey the blood in the extracorporeal blood circuit, the extracorporeal blood treatment apparatuses generally comprise an occluding hose pump, in particular a roller pump. Occluding hose pumps are also generally provided in the dialysing fluid system of extracorporeal blood treatment apparatuses. From other specialist medical fields, for example in heart bypass operations, other blood pumps are known for the operation of an extracorporeal blood circuit, in particular special centrifugal pumps designed for blood, which are characterised by causing relatively little damage to the blood.

Despite regular monitoring of the vascular access by hospital staff during extracorporeal blood treatment, there is in principle the risk of the venous puncture cannula slipping out of the patient's blood vessel unnoticed. Whereas slipping-out of the arterial cannula is associated with the sucking-in of air into the arterial hose line, the slipping-out of the venous cannula leads to the feared free flow of blood into the surroundings. If the slipping-out of the venous cannula is not detected immediately, therefore, there is the risk of the patient bleeding to death.

Various devices of differing design are known for the monitoring of the vascular access. The known monitoring devices generally rely on the safety devices which are present as standard in blood treatment apparatuses and which, in the event of an incorrect vascular access, trigger an immediate interruption to the blood flow in the extracorporeal blood circuit.

A monitoring device for a vascular access is described in International Patent Publication No. WO 99/29356 A1, wherein the strength of an electric current flowing through the fluid in the hose line is measured. U.S. Patent Publication No. 2004/0254513 describes a monitoring device, wherein the impedance between two electrodes disposed on the arterial and venous hose line is measured. A drawback is that the known devices require the creation of an electrical connection to the fluid flowing in the hose lines.

Monitoring systems are also known for monitoring both the arterial and the venous vascular access, said systems being based on a measurement of the pressure in the extracorporeal blood circuit. A drop in pressure of 20 mmHG can be assumed in practice in the event of the venous puncture cannula slipping out. Since the nominal value of the measurement value resolution lies in practice in the region of 2 mmHG with a maximum total error between 15 and 20 mmHG, the detection of a venous disconnection proves to be difficult. A monitoring system with pressure monitoring is described for example in U.S. Pat. No. 6,221,040. The known pressure monitoring makes use of a special evaluation procedure.

Monitoring devices which can detect the outflow of blood at the puncture point are described in International Patent Publication No. WO 2006/008866 A1 and U.S. Patent Publication No. 2005/0038325. These devices comprise a moisture sensor.

SUMMARY

A problem underlying the present invention is to monitor, with particularly high reliability, a vascular access and/or an extracorporeal blood circuit and/or a dialysing fluid system of an extracorporeal blood treatment apparatus without substantial changes to the blood treatment apparatus and without the use of separate components.

A solution to this problem takes place according to the present invention and advantageous embodiments described herein.

The device according to the present invention and the method according to the present invention are based on the use of a centrifugal pump for conveying blood in the extracorporeal blood circuit or dialysing fluid in the dialysing fluid system instead of an occluding pump. The centrifugal pump, which is also known by the term rotary pump, comprises a rotating pump impeller for conveying fluids. The fluid, which enters into the centrifugal pump via the suction pipe, is conveyed by the rotating pump impeller and forced to the exterior on a circuit. The kinetic energy of the fluid thereby absorbed increases the pressure inside the pump and pushes the fluid into the pressure pipe.

The present invention makes use of the special properties of the known centrifugal pumps when they are used to convey blood and/or dialysing fluid. These centrifugal pumps are characterised in that a large change in the flow rate is brought about by even a small change in the pressure difference across the pump. When mention is made below of the flow rate, this is also understood to mean any other variable correlating with the flow rate which, as it were, increases with the increase in the flow rate.

The device according to the present invention comprises a measuring unit for measuring the flow rate of the blood conveyed by the centrifugal pump in the extracorporeal blood circuit and/or of the dialysing fluid in the dialysing fluid system as well as a control and computing unit, which is constituted such that, in the event of a change in the measured flow rate of more than a predetermined amount, it is concluded that there is an incorrect vascular access or a malfunction in the extracorporeal blood circuit or dialysing fluid system. If, for example, there is a small drop in pressure in the venous blood line during the extracorporeal blood treatment, this leads to a marked increase in the flow rate of the centrifugal pump. This significant and sudden increase in the flow rate, which results from the characteristic flat delivery curve of the centrifugal pump, is used according to the present invention as a basis for the detection of an incorrect venous vascular access. With the monitoring of the flow rate of the centrifugal pump, it is possible to detect not only the slipping out of one of the two puncture cannulas from the patient's vascular system, but also nipping or kinking of the blood lines or dialysing fluid lines and a leakage of the hose lines. The flow rate can in principle be measured at any point in the extracorporeal blood circuit or dialysing fluid system.

It is advantageous that the device according to the present invention and the method according to the present invention do not make use of external components which require additional manipulations and unnecessarily restrict the patient's freedom of movement.

In a preferred embodiment of the present invention, the control and computing unit comprises a comparison unit for comparing the measured flow rate with a preset flow rate and a signal generation unit for generating a control signal when the difference between the measured flow rate and the preset flow rate is greater than a specific threshold value. This threshold value is dependent upon various factors. For example, the threshold value is dependent on the condition of the hose lines. Different threshold values can be preset depending on the various factors. A preferred embodiment provides for the imputting of data records on an input unit, said data records being characteristic of the various factors, for example of the hose set used. These data records are compared with stored data records to which specific threshold values are assigned, in order to be able to select the threshold value which corresponds to the inputted data record.

The monitoring device preferably comprises an alarm unit, which emits an acoustic and/or optical and/or tactile alarm when the control and computing unit generates the control signal.

The measuring unit for measuring the flow rate preferably comprise a flow sensor for the non-invasive measurement of the blood flow rate. The flow sensor is preferably an ultrasound flow sensor which works according to the known ultrasound Doppler method or propagation time difference method. Such ultrasound flow sensors are known to the person skilled in the art. Any other methods of measuring the flow rate known to the person skilled in the art can also be used, for example the evaluation of the motor data of the centrifugal pump, a magnetic induction flow measurement or an optical flow measurement with a laser. On the other hand, the measurement of the flow rate can also take place invasively for measurements of the flow rate in the dialysing fluid system. All flow meters known to the person skilled in the art can be used for this purpose.

The flow sensor can in principle be disposed at any point in the extracorporeal blood circuit or the dialysing fluid system, in particular on the arterial or venous blood line or the dialysing fluid supply and discharge line. In particular, the flow sensor can be integrated into the device for arterial air bubble detection which is present as standard in blood treatment apparatuses.

The apparatus for extracorporeal blood treatment according to the present invention comprises the monitoring device according to the present invention. A preferred embodiment of the blood treatment apparatus according to the present invention makes provision such that the control unit of the blood treatment apparatus intervenes in the machine control when the control and computing unit of the monitoring device generates a control signal. The control unit is preferably constituted such that the centrifugal pump disposed in the extracorporeal blood circuit is stopped as an intervention into the machine control. Moreover, at least one shut-off element disposed in or on the venous blood line is preferably closed. Both the arterial and the venous hose clamp are preferably closed. In the event of an incorrect vascular access, for example when the venous puncture cannula has slipped out or a leakage is present in the hose system, the free flow of blood into the surroundings is thus immediately stopped.

An exemplary embodiment of the present invention is described in detail below by reference to the accompanying drawings.

DETAILED DESCRIPTION

The device according to the present invention for monitoring a vascular access or the extracorporeal blood circuit or dialysing fluid system can form a separate unit or can also be a component of the extracorporeal blood treatment apparatus. If the monitoring device according to the present invention is a component of the blood treatment apparatus, the monitoring device according to the present invention can make use of specific subassemblies or components which are in any case present in the blood treatment apparatus.

An extracorporeal blood treatment apparatus A is described below, which comprises a device for monitoring the vascular access and the extracorporeal blood circuit and the dialysing fluid system. A monitoring device solely for monitoring the vascular access or the extracorporeal blood circuit or the dialysing fluid system can however also be provided.

Figure 1:
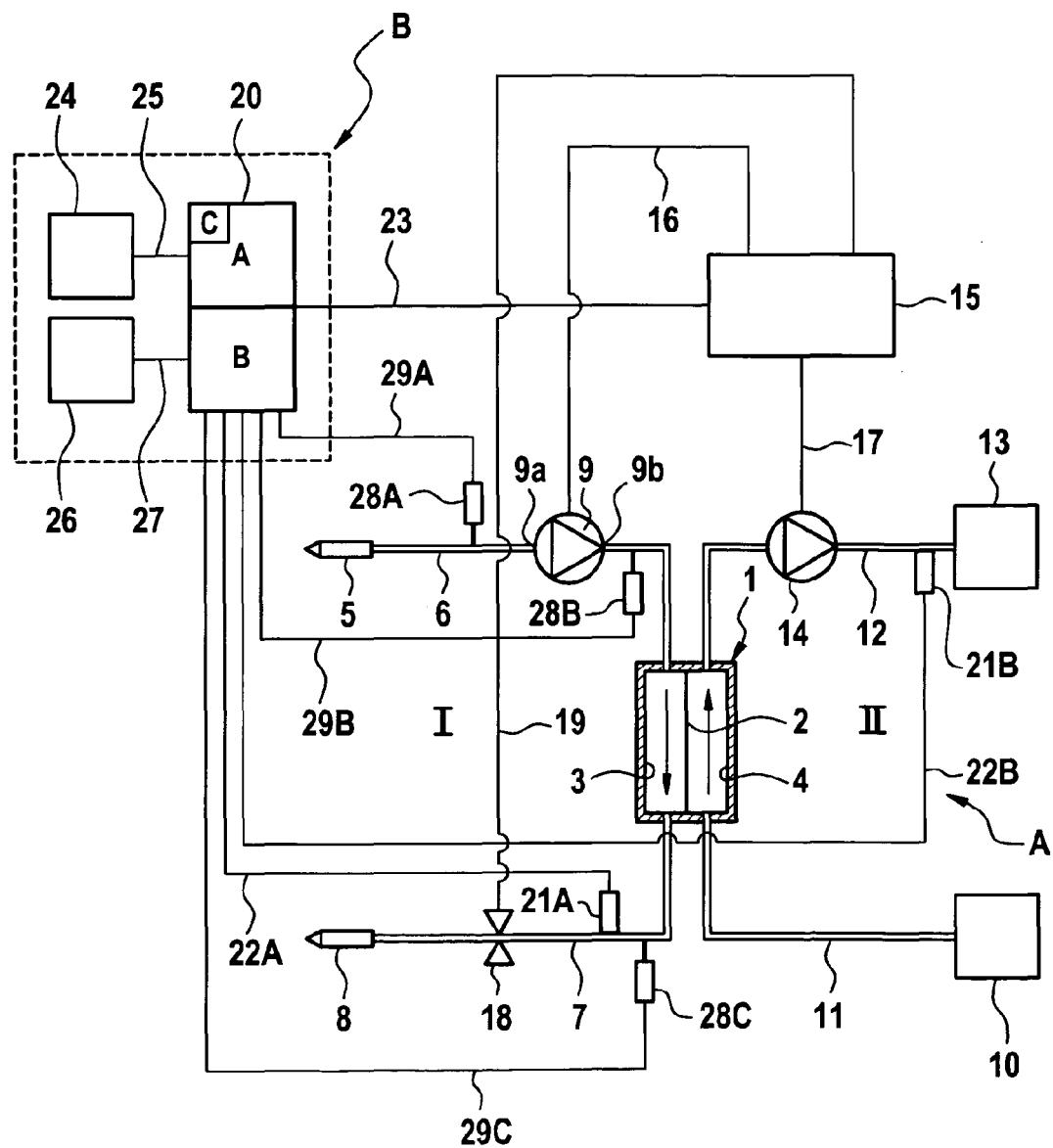
FIG. 1 shows the main components of an exemplary extracorporeal blood treatment apparatus according to the present invention, with a device according to the present invention for monitoring a vascular access or the extracorporeal blood circuit or dialysing fluid system.

FIG. 1 shows only the main components of an exemplary blood treatment apparatus in a schematic representation, since blood treatment apparatuses as such are known to the person skilled in the art.

The blood treatment apparatus is a known haemodialysis apparatus, which comprises a dialyser 1 which is divided by a semi-permeable membrane 2 into a blood chamber 3 and a dialysing fluid chamber 4. Connected by an arterial puncture cannula 5 to the shunt or a fistula of the patient is arterial hose line 6 which leads to the inlet of blood chamber 3 of the dialyser. Leading away from the outlet of blood chamber 3 of the dialyser is a venous hose line 7, which is connected by a venous puncture cannula 8 to the shunt or the fistula. The blood is conveyed in extracorporeal blood circuit I by a centrifugal pump 9, which is provided on arterial hose line 6. The centrifugal pump is a pump specially designed for blood, which is characterised by causing little damage to the blood.

Dialysing fluid system II of the haemodialysis apparatus comprises a dialysing fluid source 10, to which a dialysing fluid supply line 11 is connected, which leads to the inlet of dialysing fluid chamber 4 of the dialyser. Leading away from the outlet of dialysing fluid chamber 4 of the dialyser is a dialysing fluid discharge line 12 which leads to an outlet 13. The dialysing fluid is conveyed in the dialysing fluid circuit by a dialysing fluid pump 14, which is disposed on dialysing fluid discharge line 12. In the present example embodiment, the monitoring device is also used to monitor the dialysing fluid system. Dialysing fluid pump 14 is therefore also a centrifugal pump. This is not necessary, however, if the monitoring device is used solely to monitor the vascular access or the extracorporeal blood circuit.

The control of the dialysis apparatus is assumed by a central control unit 15, which controls blood pump and dialysing-fluid pump 9, 14 via control lines 16, 17. Located downstream of blood chamber 3 of the dialyser on venous hose line 7 is an electromagnetically operated hose clamp 18, which can be opened or closed by central control unit 15 via a further control line 19. When venous hose clamp 18 is closed, the fluid flow in extracorporeal blood circuit I is interrupted, so that blood cannot pass into the surroundings.

Monitoring device B comprises a control and computing unit 20, which is represented in FIG. 1 as a separate unit. Control and computing unit 20 can however also be a component of central control unit 15 of the blood treatment apparatus.

Moreover, monitoring device B comprises a measuring unit for measuring the flow rate of the blood conveyed in extracorporeal blood circuit I by centrifugal pump 9 and a measuring unit for measuring the flow rate of the dialysing fluid conveyed in a dialysing fluid system II by centrifugal pump 14. The measuring unit for measuring the flow rate in extracorporeal blood circuit I comprises a flow sensor 21A, which in the present example embodiment is disposed downstream of dialysing fluid chamber 3 of dialyser 1 and upstream of hose clamp 18 on venous blood line 7, whilst the measuring unit for measuring the flow rate of the conveyed dialysing fluid comprises a flow sensor 21B, which is disposed downstream of dialysing fluid pump 14. In the present example embodiment, flow sensors 21A and 21B are ultrasound flow sensors for the non-invasive measurement of the flow rate of the blood and the dialysing fluid respectively. The measured values of ultrasound flow sensors 21A and 21B are received by control and computing unit 20 via data lines 22A and 22B.

Control and computing unit 20 comprises a comparison unit 20A for comparing the measured flow rate with a preset flow rate. Moreover, control and computing unit 20 comprises a signal generation unit 20B for generating a control signal which is received by central control unit 15 via a data line 23.

A specific blood flow rate is set for the extracorporeal blood treatment by the doctor in charge. Central control unit 15 of the blood treatment apparatus sets speed n of centrifugal pump 9 such that the blood in extracorporeal blood circuit I is conveyed at a preset flow rate. The preset flow rate is measured by flow sensor 21A. This flow rate corresponds to the flow rate of centrifugal pump 9, which is preset as a reference value in control and computing unit 20. This flow rate is therefore referred to as the preset flow rate. The flow rate of the blood is now continuously monitored during the extracorporeal blood treatment. The flow rate measured by flow sensor 21A is constantly compared with the flow rate previously preset as a reference value. The difference between the measured flow rate and the preset flow rate is worked out. If the difference is greater than a specific threshold value, control and computing unit 20 generates a control signal, which is received by central control unit 15 via data line 23.

Figure 2:
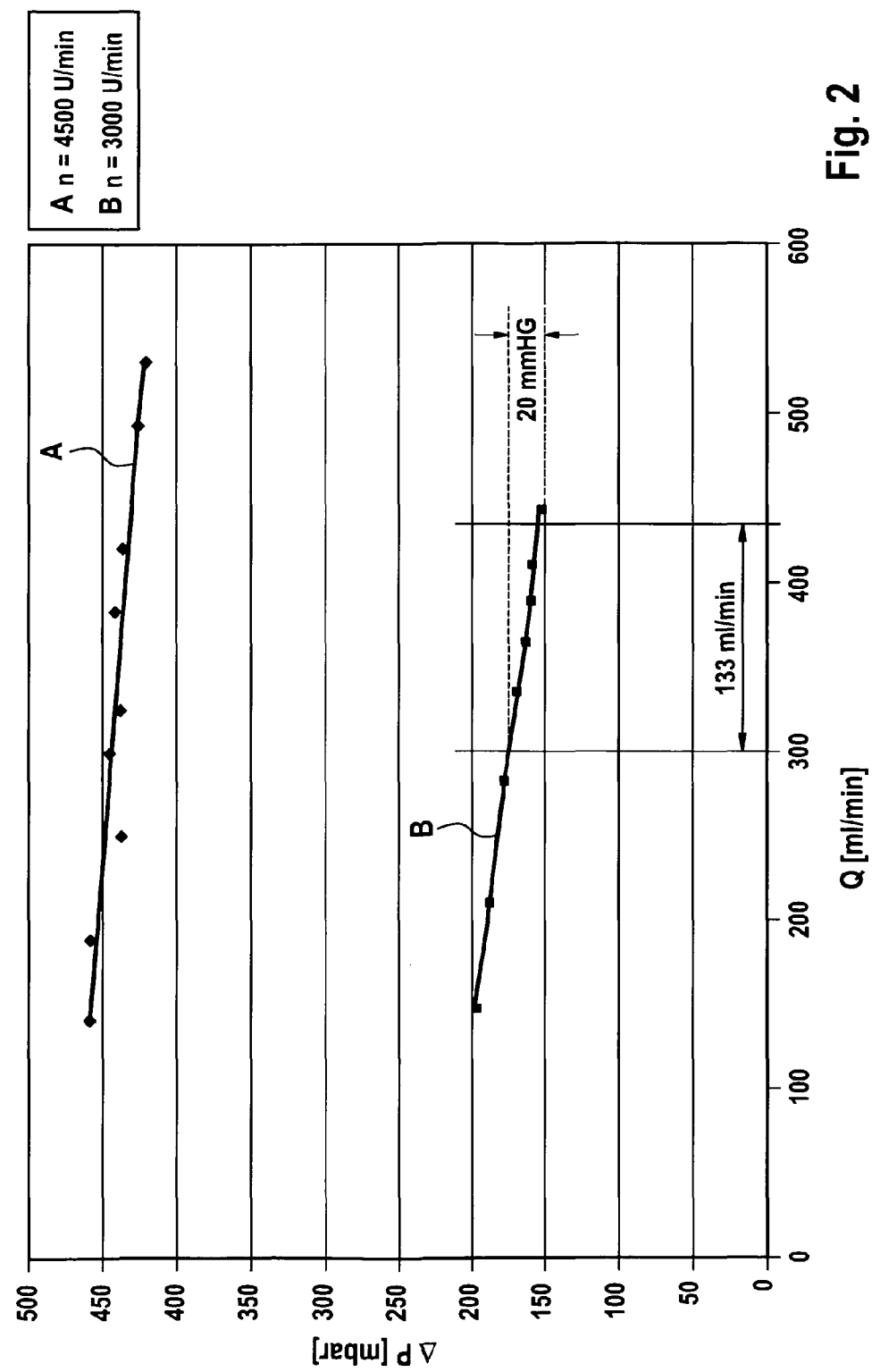
FIG. 2 shows the basic course of the pressure difference across the exemplary centrifugal pump present in the extracorporeal blood circuit as a function of the blood flow.

FIG. 2 shows the pressure difference between inlet 9a and outlet 9b of an exemplary centrifugal pump 9 as a function of flow rate Q. The slipping-out of venous puncture cannula 8 leads to a change in pressure ΔP of 20 mmHG across centrifugal pump 9 in extracorporeal blood circuit I. FIG. 2 shows that, with a speed n of 3000 revs/min, blood flow rate Q of 300 ml/min increases by 133 ml/min. At 4500 revs/min, a volume flow increase of 235 ml/min can be seen. The two characteristic curves (characteristic curve A 4500 revs/min and characteristic curve B 3000 revs/min) show that even a small change in pressure ΔP of 20 mmHG leads to a significant increase in flow rate Q.

Control and computing unit 20 compares the difference between the measured flow rate and the preset flow rate with a specific threshold value. If the difference is greater than the threshold value, i.e. a significant increase in the flow rate is recorded, an incorrect vascular access is assumed and the control signal is generated.

Monitoring device B comprises an alarm unit 24, which receives the control signal of control and computing unit 20 via a data line 25. Alarm unit 24 then emits an acoustic and/or optical and/or tactile alarm. The alarm unit can however also be a component of the blood treatment apparatus. When central control unit 15 of the blood treatment apparatus receives the control signal of control and computing unit 20, central control unit 15 stops centrifugal pump 9 immediately and immediately closes hose clamp 18, so that the free flow of blood into the surroundings is immediately stopped.

Monitoring device B also comprises an input unit 26, which is connected via a data line 27 to control and computing unit 20. Input unit 26 can also be a component of the blood treatment apparatus.

Various parameters can be inputted on input unit 26 of monitoring device B, said parameters including for example the data describing employed hose system 6, 7, which indicate for example the internal diameter, the wall thickness or the material of the hose lines. The data input can take place manually or automatically, for example by means of a barcode, matrix code, RFID etc. Control and computing unit 20 comprises a memory 20C, in which specific threshold values for the monitoring of the vascular access are assigned to various data records. Control and computing unit 20 compares the data records inputted on input unit 26 with the assigned data records and selects the threshold value that corresponds to the inputted data record. This ensures that different threshold values for the monitoring of the vascular access can be made available for different hose lines.

The threshold value can in principle also be dynamically variable. On the one hand, the threshold value can be preselected as fixed by the user, for example before the start of the treatment. On the other hand, the threshold value can also be adapted during the treatment. The adaptation can also take place automatically. For example, slow changes in the flow can occur due to viscosity changes in the blood or also a change in the filter properties. In order not to trigger an alarm in such cases, the threshold value can be automatically adapted accordingly. The alarm limits for abrupt changes in the flow rate can also be "carried along" until a preset limit is reached. "Preset" is understood in this connection to mean that the threshold value is present or made available in the evaluation unit before its use.

The monitoring of the flow rate of the dialysing fluid in order to detect a malfunction in dialysing fluid system II takes place in a similar manner to the monitoring of the blood flow rate, wherein the dialysing fluid flow rate measured by flow sensor 21B is compared with a preset flow rate. If the difference between the measured and preset flow rate is greater than a specific threshold value, it is concluded that there is a malfunction in the dialysing fluid system. This malfunction may again lie in a kinked or nipped hose line or a leakage.

In a preferred embodiment, the rate of change of the flow rates in the hose lines is monitored, wherein the hose lines may be arterial and venous blood line 6, 7 or dialysing fluid supply or discharge line 11, 12. The rate of change of the flow rate is compared with a preset threshold value. It is concluded that there is a malfunction especially in the case of a sudden change in the flow rate. In addition to the monitoring of the flow rates, the pressure characteristics in the hose lines can also be monitored. It is thus possible to distinguish between specific malfunctions, for example between a disconnection of a cannula or a leakage or the clogging up of dialyser 1. In a preferred embodiment, pressure sensors for measuring the pressure in the hose lines are provided for this purpose.

FIG. 1 shows a pressure sensor 28A for measuring the pressure in arterial blood line 6 upstream of blood pump 9 and a pressure sensor 28B for measuring the pressure in arterial blood line 6 downstream of blood pump 9 as well as a pressure sensor 28C for measuring the pressure in venous blood line 7. Pressure sensor 28A is connected via a data line 29A, pressure sensor 28B is connected via a data line 29B and pressure sensor 28C is connected via a data line 29C to control and computing unit 20.

In the preferred embodiment, control and computing unit 20 is constituted such that a distinction can be made between the cases stated below.

If the blood flow rate in extracorporeal blood circuit I measured by flow sensor 21A falls at a rate which is greater than a preset first threshold value, and the pressure measured by pressure sensor 28A upstream of blood pump 9 falls below a preset threshold value, control and computing unit 20 concludes that the blood line is kinked or nipped.

If the blood flow rate in extracorporeal blood circuit I measured by flow sensor 21A falls at a rate which is greater than a preset second threshold value, and the pressure measured by pressure sensor 28B downstream of blood pump 9 increases above a preset threshold value, control and computing unit 20 concludes that the blood line is kinked or nipped.

If the blood flow rate in extracorporeal blood circuit I measured by flow sensor 21A falls at a rate which is greater than a preset third threshold value which is less than the aforementioned first threshold value, i.e. the flow rate falls more slowly, and the pressure measured by pressure sensor 28B downstream of blood pump 9 increases above a preset threshold value, control and computing unit 20 concludes that dialyser 1 is clogged up.

If the blood flow rate in extracorporeal blood circuit I measured by flow sensor 21A increases at a rate which is greater than a preset fourth threshold value, i.e. the flow rate increases rapidly, and the pressure measured by pressure sensor 28C in venous blood line 7 remains constant or falls, control and computing unit 20 concludes that a disconnection of venous cannula 8 is present.

The invention claimed is:

1. A device for monitoring an extracorporeal blood treatment apparatus with an extracorporeal blood circuit having an arterial blood line with an arterial patient connection and a venous blood line with a venous patient connection, and a dialyzing fluid system, wherein a dialyzer is in fluid communication with the extracorporeal blood circuit and the dialyzing fluid system, and a centrifugal pump for conveying blood in the extracorporeal blood circuit is disposed in the arterial blood line between the dialyzer and the arterial patient connection of the extracorporeal blood circuit, the device comprising a flow sensor configured to measure a flow rate Q of the blood conveyed by the centrifugal pump in the extracorporeal blood circuit, wherein the flow sensor is positioned to measure flow in the venous blood line, pressure sensors comprising a first arterial line pressure sensor, a second arterial line pressure sensor, and a venous line pressure sensor, wherein the first arterial line pressure sensor is configured to measure the pressure in the arterial blood line between the arterial patient connection and the centrifugal pump, and the second arterial line pressure sensor is configured to measure the pressure in the arterial blood line between the centrifugal pump and the dialyzer, and a control and computing unit configured to monitor the rate of change of the measured flow rate such that, in the event that the rate of change of the measured flow rate is more than a specific threshold value, at least one of an incorrect vascular access or a malfunction in the extracorporeal blood circuit is determined, wherein the control and computing unit is further configured to:

distinguish between specific malfunctions based on (1) the rate of the change of the measured flow rate, (2) whether the flow rate is dropping or increasing, (3) the pressure measured by at least one of the pressure sensors, and (4) whether the pressure measured is dropping, increasing, or remaining constant;

compare the rate of change of the measured flow rate with the specific threshold value; and determine that the venous patient connection has slipped out when the rate of change of the measured flow rate is more than the specific threshold value and there is a drop in pressure in the venous blood line.

2. A device for monitoring an extracorporeal blood treatment apparatus with an extracorporeal blood circuit, and a dialyzing fluid system having a dialyzing fluid supply line and a dialyzing fluid discharge line, wherein a centrifugal pump for conveying dialyzing fluid is disposed in one of the dialyzing fluid supply line or the dialyzing fluid discharge line of the dialyzing fluid system, the device comprising:

a flow sensor configured to measure a flow rate Q of the dialyzing fluid conveyed by the centrifugal pump in the dialyzing fluid system, at least one dialyzing fluid pressure sensor configured to measure pressure in (a) the dialyzing fluid discharge line, or (b) both the dialyzing fluid supply line and the dialyzing fluid discharge line, and a control and computing unit configured to monitor the rate of change of the measured flow rate such that, in the event that the rate of change of the measured flow rate is more than a specific threshold value, a malfunction in the dialyzing fluid system is determined, the control and computing unit comprising an input unit and a comparison unit, the input unit being configured to input data records characteristic of a hose set used, the comparison unit being configured to compare the data records to stored data records to which specific threshold values are assigned, to determine the specific threshold value, wherein the control and computing unit is further configured to distinguish between specific malfunctions based on the rate of the change of the measured flow rate, whether the flow rate is dropping or increasing, the pressure measured by the at least one dialyzing fluid pressure sensor, and whether the dialyzing fluid pressure measured is dropping, increasing, or remaining constant.

3. A method for monitoring an extracorporeal blood treatment apparatus with an extracorporeal blood circuit having an arterial blood line with an arterial patient connection and a venous blood line with a venous patient connection, and a dialyzing fluid system, wherein a dialyzer is in fluid communication with the extracorporeal blood circuit and the dialyzing fluid system, and a centrifugal pump for conveying blood in the extracorporeal blood circuit is disposed in the arterial blood line between the dialyzer and the arterial patient connection, the method comprising:

measuring a flow rate Q of the blood conveyed by the centrifugal pump in the extracorporeal blood circuit and monitoring a rate of change of the flow rate Q, measuring a pressure in the arterial blood line and measuring a pressure in the venous blood line, wherein the measuring of pressure in the arterial blood line comprises i) measuring pressure in the arterial blood line between the arterial patient connection and the centrifugal pump or ii) measuring pressure in the arterial blood line between the centrifugal pump and the dialyzer, determining at least one of an incorrect vascular access or a malfunction in the extracorporeal blood circuit in the event that the rate of change of the measured flow rate Q is more than a specific threshold value, distinguishing between specific malfunctions based on the rate of change, whether the flow rate is dropping or increasing, the measured pressure in the arterial blood line or in the venous blood line, and whether the pressure measured is dropping, increasing, or remaining constant, and determining that the venous patient connection has slipped out when the rate of change of the measured flow rate is more than a specific threshold value and there is a drop in pressure in the venous blood line.

4. A method for monitoring an extracorporeal blood treatment apparatus with an extracorporeal blood circuit having an arterial blood line with an arterial patient connection and a venous blood line with a venous patient connection, and a dialyzing fluid system having a dialyzing fluid supply line and a dialyzing fluid discharge line, wherein a centrifugal pump for conveying dialyzing fluid is disposed in one of the dialyzing fluid supply line or the dialyzing fluid discharge line of the dialyzing fluid system, the method comprising:

inputting data records characteristic of a hose set being used, comparing the data records to stored data records to which specific threshold values are assigned, determining, from the comparison, a specific threshold value to be used, measuring flow rate Q of the dialyzing fluid conveyed by the centrifugal pump in the dialyzing fluid system and monitoring a rate of change of the flow rate Q, measuring a dialyzing fluid pressure in at least the dialyzing fluid discharge line, determining a malfunction in the dialyzing fluid system in the event that the rate of change of the measured flow rate Q is more than the specific threshold value, and distinguishing between specific malfunctions based on the rate of change, whether the rate of change is dropping or increasing, the measured dialyzing fluid pressure, and whether the measured dialyzing fluid pressure is dropping, increasing, or remaining constant.

5. The device according to claim 1, wherein the control and computing unit is further configured to generate a control signal when the rate of change of the measured flow rate is greater than the specific threshold value.

6. The device according to claim 2, wherein the control and computing unit is further configured to compare the rate of change of the measured flow rate with the specific threshold value and to generate a control signal when the rate of change of the measured flow rate is greater than the specific threshold value.

7. An apparatus for extracorporeal blood treatment with an extracorporeal blood circuit, comprising:

an extracorporeal blood circuit having an arterial blood line with an arterial patient connection and a venous blood line with a venous patient connection, wherein a centrifugal pump configured to convey blood in the extracorporeal blood circuit is disposed in the arterial blood line, a dialyzing fluid system, a dialyzer in fluid communication with the extracorporeal blood circuit and the dialyzing fluid system, wherein the centrifugal pump is disposed in the arterial blood line between the dialyzer and the arterial patient connection, and the monitoring device according to claim 1.

8. An apparatus for extracorporeal blood treatment with an extracorporeal blood circuit and a dialyzing fluid system, comprising:

a dialyzing fluid supply line and a dialyzing fluid discharge line, wherein a centrifugal pump configured to convey dialyzing fluid is disposed in one of the dialyzing fluid supply line or the dialyzing fluid discharge line of the dialyzing fluid system, and the monitoring device according to claim 2.

9. The apparatus according to claim 7, further comprising a central control unit configured such that the control unit intervenes in the machine control when the control and computing unit of the monitoring device generates a control signal.

10. The apparatus according to claim 9, wherein the control unit of the blood treatment apparatus is configured such that the centrifugal pump disposed in the extracorporeal blood circuit is stopped as an intervention into the machine control.

11. The apparatus according to claim 9, wherein the control unit of the blood treatment apparatus is configured such that a shut-off element disposed in or on the venous blood line is closed as an intervention in the machine control.

12. The apparatus according to claim 7, wherein the centrifugal pump is disposed in the arterial blood line.

13. The device according to claim 1, wherein the control and computing unit is configured to determine that the arterial or venous blood line is kinked or nipped if the measured flow rate falls at a rate that is greater than a preset first flow rate threshold value and the pressure measured by the first arterial pressure sensor falls below a preset first pressure threshold value.

14. The device according to claim 1, wherein the control and computing unit is configured to determine that the dialyzer is clogged if the measured flow rate falls at a rate that is greater than a preset third flow rate threshold value that is less than the preset first flow rate threshold value, and the pressure measured by the second arterial pressure sensor increases above a preset third pressure threshold value.

15. The device according to claim 1, wherein the control and computing unit is configured to determine that:
the arterial or venous blood line is kinked or nipped if the measured flow rate falls at a rate that is greater than a preset second flow rate threshold value and the pressure measured by the second arterial pressure sensor increases above a preset second pressure threshold value.

16. The device according to claim 1, wherein the venous line pressure sensor is configured to measure the pressure in the venous blood line between the dialyzer and the venous patient connection, and the control and computing unit is configured to determine that a disconnection of the venous patient connection is present if the measured flow rate increases at a rate that is greater than a preset fourth flow rate threshold value, and the pressure measured by the venous pressure sensor remains constant or falls.

17. The device according to claim 1, wherein the control and computing unit comprises an input unit and a comparison unit, the input unit being configured to input data records characteristic of a hose set used, the comparison unit being configured to compare the data records to stored data records to which specific threshold values are assigned, to determine the specific threshold value.

* * * * *